United States Patent
Marsden et al.

(10) Patent No.: US 11,129,581 B2
(45) Date of Patent: Sep. 28, 2021

(54) ANTI-SCATTER COLLIMATOR FOR RADIATION IMAGING MODALITIES

(71) Applicant: Analogic Corporation, Peabody, MA (US)

(72) Inventors: Lane Howitt Marsden, Reading, MA (US); Vladan Ristanovic, Saugus, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 16/485,764

(22) PCT Filed: Feb. 16, 2017

(86) PCT No.: PCT/US2017/018123
§ 371 (c)(1),
(2) Date: Aug. 13, 2019

(87) PCT Pub. No.: WO2018/151727
PCT Pub. Date: Aug. 23, 2018

(65) Prior Publication Data
US 2020/0046306 A1    Feb. 13, 2020

(51) Int. Cl.
*A61B 6/00*    (2006.01)
*A61B 6/03*    (2006.01)
(Continued)

(52) U.S. Cl.
CPC ............ *A61B 6/4291* (2013.01); *A61B 6/035* (2013.01); *A61B 6/4233* (2013.01); *G21K 1/025* (2013.01); *A61B 6/025* (2013.01)

(58) Field of Classification Search
CPC ..... A61B 6/4291; A61B 6/035; A61B 6/4233; A61B 6/025; A61B 6/032; A61B 6/06; G21K 1/025
See application file for complete search history.

(56) References Cited

U.S. PATENT DOCUMENTS 4,780,904 A    10/1988    Winter
5,099,134 A *    3/1992    Hase ...................... G21K 1/025
                                                                250/363.1
(Continued)

FOREIGN PATENT DOCUMENTS

WO    2018/151727 A1    8/2018

OTHER PUBLICATIONS

Written Opinion of the International Searching Authority for PCT Application No. PCT/US2017/018123 dated Nov. 30, 2017, 8 pages.
(Continued)

*Primary Examiner* — Kiho Kim
(74) *Attorney, Agent, or Firm* — TraskBritt

(57) ABSTRACT

Among other things, an anti-scatter collimator is provided including a first layer defining a first retaining member at a first surface. A second layer defines a second retaining member at a first surface that faces the first surface of the first layer. A septum is disposed between the first layer and the second layer and physically contacts the first retaining member and the second retaining member. The first retaining member and the second retaining member maintain a position of the septum relative to the first layer and the second layer. The septum has a third attenuation coefficient that is greater than a first attenuation coefficient of the first layer and a second attenuation coefficient of the second layer. An end support is attached to the first layer and to the second layer. The end support borders an end of the septum.

20 Claims, 12 Drawing Sheets

(51) Int. Cl.
*G21K 1/02*    (2006.01)
*A61B 6/02*    (2006.01)

(56) References Cited

U.S. PATENT DOCUMENTS

| | | | |
|---|---|---|---|
| 5,721,761 | A | 2/1998 | Ferlic et al. |
| 7,526,070 | B2 * | 4/2009 | Igarashi ................. A61B 6/032 378/147 |
| 7,526,875 | B2 * | 5/2009 | Freund ................... G21K 1/025 33/645 |
| 2002/0064252 | A1 | 5/2002 | Igarashi et al. |
| 2003/0223548 | A1 | 12/2003 | Galish et al. |
| 2005/0135562 | A1 * | 6/2005 | Freund ................... G21K 1/025 378/147 |
| 2006/0145081 | A1 * | 7/2006 | Hawman ................ G21K 1/025 250/363.1 |
| 2007/0096030 | A1 * | 5/2007 | Li ........................... G01T 1/243 250/370.09 |
| 2009/0225955 | A1 | 9/2009 | Igarashi et al. |
| 2011/0164727 | A1 | 7/2011 | Tonami |
| 2015/0162107 | A1 * | 6/2015 | Kato ..................... G21K 1/025 378/19 |
| 2019/0099149 | A1 * | 4/2019 | Li ......................... A61B 6/032 |

OTHER PUBLICATIONS

International Search Report for PCT Application No. PCT/US2017/018123 dated Nov. 30, 2017, 6 pages.

\* cited by examiner

ANTI-SCATTER COLLIMATOR FOR RADIATION IMAGING MODALITIES

CROSS-REFERENCE TO RELATED APPLICATIONS

This application is a national phase entry under 35 U.S.C. § 371 of International Patent Application PCT/US2017/018123, filed Feb. 16, 2017, designating the United States of America and published as International Patent Publication WO 2018/151727 A1 on Aug. 23, 2018.

TECHNICAL FIELD

The present application relates to an anti-scatter collimator for radiation imaging modalities (e.g., imaging modalities that utilize radiation to examine an object). It finds particular application in the context of computed tomography (CT) scanners. However, the features described herein are not intended to be limited to CT applications and may be used for other radiation imaging applications, such as line-scan systems and tomosynthesis systems (e.g., mammography systems).

BACKGROUND

Today, CT and other radiation imaging modalities (e.g., mammography, digital radiography, single-photon emission computed tomography, etc.) are useful to provide information, or images, of interior aspects of an object under examination. Generally, the object is exposed to radiation (e.g., X-rays, gamma rays, etc.), and an image(s) is formed based upon the radiation absorbed and/or attenuated by the interior aspects of the object, or rather an amount of radiation photons that is able to pass through the object. Typically, highly dense aspects of the object (or aspects of the object having a composition comprised of higher atomic number elements) absorb and/or attenuate more radiation than less dense aspects, and thus an aspect having a higher density (and/or high atomic number elements), such as a bone or metal, for example, will be apparent when surrounded by less dense aspects, such as muscle or clothing.

Radiation imaging modalities generally comprise, among other things, one or more radiation sources (e.g., an X-ray source, gamma-ray source, etc.) and a detector array comprised of a plurality of pixels (also referred to as cells) that are respectively configured to convert radiation that has traversed the object into signals that can be processed to produce the image(s). As an object is passed between the radiation source(s) and the detector array, radiation is absorbed/attenuated by the object, causing changes in the amount/energy of detected radiation. Using information derived from the detected radiation, radiation imaging modalities are configured to generate images that can be used to detect items within the object that can be of particular interest (e.g., body characteristics, threat items, etc.). These images can be two-dimensional images or three-dimensional images.

In an ideal environment, the radiation that is detected by a pixel corresponds to primary radiation that strikes the pixel on a straight axis from a focal spot of the radiation source. However, some of the radiation that impinges upon the object is scattered, and deviates from a straight path. Scattered radiation, also referred to as secondary radiation, that is detected by a pixel increases noise and reduces the quality of an image produced based upon the detector signal.

To reduce the possibility of scattered radiation impacting a pixel of the detector array, anti-scatter collimators can be inserted between the examination region and the detector array. These anti-scatter collimators comprise anti-scatter plates, also referred to as septa, which are configured to absorb scattered radiation while allowing primary radiation to pass through the collimator and be detected by a pixel of the detector array. The septa are aligned with respect to the radiation source and the detector array to allow the primary radiation to pass through while absorbing the secondary radiation. Systems with large septa utilize fixation structures to maintain the septa in place. Despite the use of these fixation structures, unintended vibration and motion of the septa can occur, which results in reduced image quality. Moreover, assembly of the septa with the fixation structures can be resource intensive (e.g., time intensive), which increases manufacturing costs.

BRIEF SUMMARY

Aspects of the present application address the above matters, and others. According to one aspect, an anti-scatter collimator comprises a first layer defining a first retaining member at a first surface. The first layer has a first attenuation coefficient. The anti-scatter collimator comprises a second layer defining a second retaining member at a first surface that faces the first surface of the first layer. The second layer has a second attenuation coefficient. A septum is disposed between the first layer and the second layer and physically contacts the first retaining member and the second retaining member. The first retaining member and the second retaining member maintain a position of the septum relative to the first layer and the second layer. The septum has a third attenuation coefficient that is greater than the first attenuation coefficient and the second attenuation coefficient. An end support is attached to the first layer and to the second layer. The end support borders an end of the septum.

According to another aspect, an anti-scatter collimator comprises a first layer defining a first retaining member at a first surface. The first layer has a first attenuation coefficient. A second layer defines a second retaining member at a first surface that faces the first surface of the first layer. The second layer has a second attenuation coefficient. A plurality of septa are disposed between the first layer and the second layer and physically contacts the first retaining member and the second retaining member. The first retaining member and the second retaining member maintain a position of each of the plurality of septa relative to the first layer and the second layer. A pitch between a first septum of the plurality of septa and a second septum of the plurality of septa near the first layer is different than a second pitch between the first septum and the second septum of the plurality of septa near the second layer.

According to another aspect, a computed tomography (CT) imaging modality comprises a radiation source configured to emit radiation. A detector array is configured to detect at least a portion of the radiation. An anti-scatter collimator is disposed between the radiation source and the detector array. The anti-scatter collimator comprises a first layer defining a first retaining member at a first surface. The first layer has a first attenuation coefficient. A second layer defines a second retaining member at a first surface that faces the first surface of the first layer. The second layer has a second attenuation coefficient. A septum is disposed between the first layer and the second layer and physically contacts the first retaining member and the second retaining member. The first retaining member and the second retaining member maintain a position of the septum relative to the first layer and the second layer. The septum has a third attenuation coefficient that is greater than the first attenuation coefficient and the second attenuation coefficient. An end support is attached to the first layer and to the second layer. The end support borders an end of the septum.

Those of ordinary skill in the art will appreciate still other aspects of the present application upon reading and understanding the appended description.

BRIEF DESCRIPTION OF THE DRAWINGS

The application is illustrated by way of example and not limitation in the figures of the accompanying drawings, in which like references generally indicate similar elements and in which.

DETAILED DESCRIPTION

Figure 1:
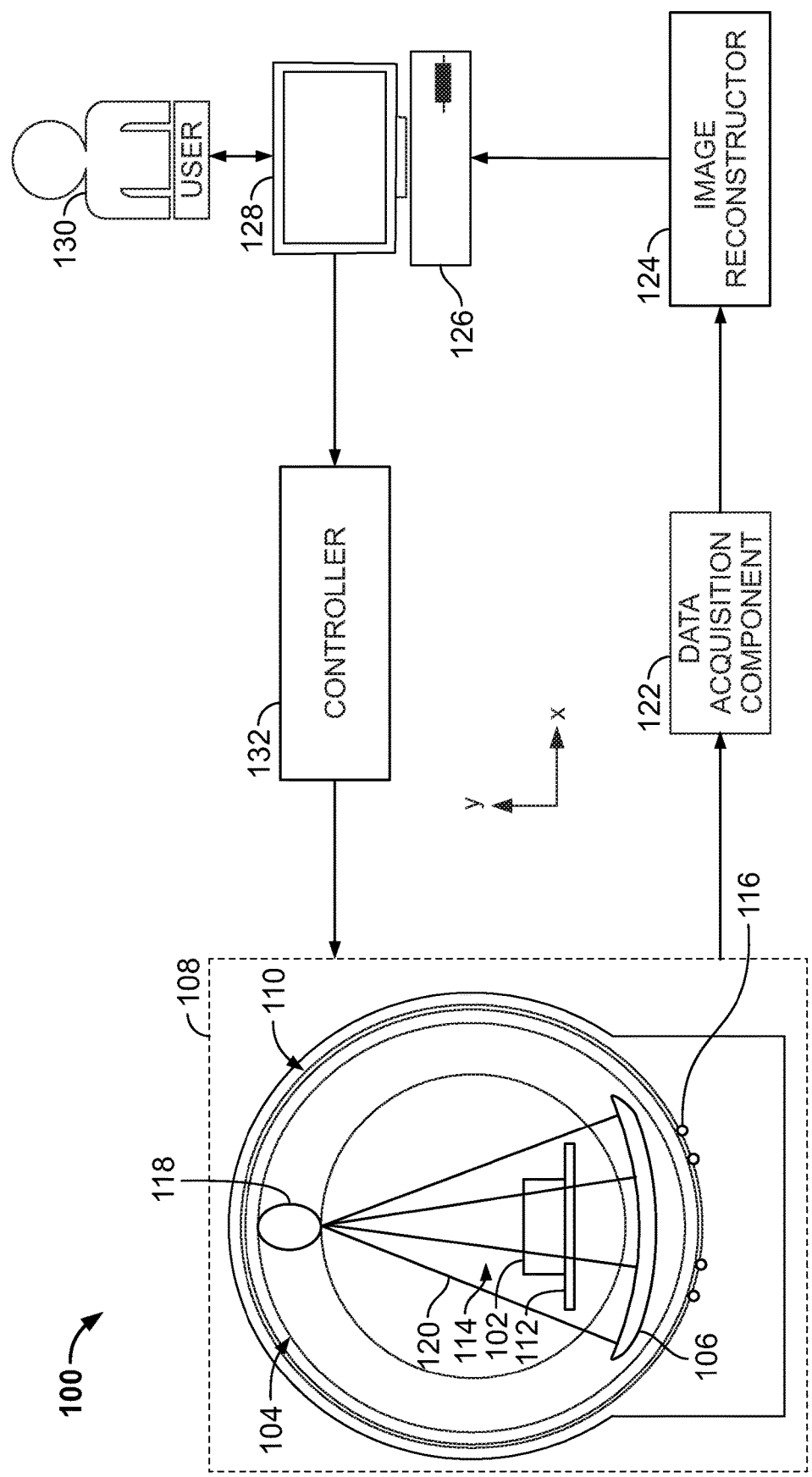
FIG. 1 illustrates an example environment of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It can be evident, however, that the claimed subject matter can be practiced without these specific details. In other instances, structures and devices are illustrated in block diagram form in order to facilitate describing the claimed subject matter.

The present disclosure relates to an anti-scatter collimator that may be positioned between a radiation source and a detector array. The anti-scatter collimator has a first layer, a second layer, and a plurality of septa disposed between the first layer and the second layer. The first layer has a first retaining member for maintaining a position of the septa relative to the first layer, while the second layer has a second retaining member for maintaining a position of the septa relative to the second layer. In this way, each septum of the plurality of septa is sandwiched between the first layer and the second layer (e.g., in a direction of travel between the radiation source and the detector array) to fixedly secure the position of each septum.

The plurality of septa can be spaced apart to define transmission channels through which primary radiation can travel substantially unimpeded. By being positioned between the radiation source and the detector array, radiation transmitted from the radiation source passes through the anti-scatter collimator prior to being received by the detector array. Due to the orientation of the anti-scatter collimator relative to the radiation source and the detector array, the septa can absorb or attenuate scattered (or secondary) radiation while primary radiation can pass through the transmission channels to the detector array.

FIG. 1 is an illustration of an example environment 100 comprising an example radiation imaging modality that can be configured to generate data (e.g., images) representative of an object 102 or aspect(s) thereof under examination. It will be appreciated that the features described herein can find applicability to other imaging modalities besides the example computed tomography (CT) scanner illustrated in FIG. 1. Moreover, the arrangement of components and/or the types of components included in the example environment 100 are for illustrative purposes only. For example, the rotating structure 104 (e.g., a rotating gantry) can comprise additional components to support the operation of a radiation source 118 and/or detector array 106, such as a cooling unit, power units, etc. As another example, a data acquisition component 122 can be comprised within and/or attached to the detector array 106.

In the example environment 100, an examination unit 108 of the imaging modality is configured to examine one or more objects 102. The examination unit 108 can comprise a rotating structure 104 and a (stationary) support structure 110, also referred to herein as a frame, which can encase and/or surround at least a portion of the rotating structure 104 (e.g., as illustrated with an outer, stationary ring, surrounding an outside edge of an inner, rotating ring). During an examination of the object(s) 102, the object(s) 102 can be placed on an object support 112, such as a bed or conveyor belt, for example, that is selectively positioned in an examination region 114 (e.g., a hollow bore in the rotating structure 104), and the rotating structure 104 can be rotated and/or supported about the object(s) 102 by a rotator 116, such as a bearing, motor, belt drive unit, drive shaft, chain, roller truck, etc.

The rotating structure 104 can surround a portion of the examination region 114 and can comprise one or more radiation sources 118 (e.g., an ionizing X-ray source, gamma radiation source, etc.) and a detector array 106 that is mounted on a substantially diametrically opposite side of the rotating structure 104 relative to the radiation source(s) 118.

During an examination of the object(s) 102, the radiation source(s) 118 emits fan or cone shaped radiation 120 from a focal spot(s) of the radiation source(s) 118 (e.g., a region within the radiation source(s) 118 from which radiation 120 emanates) into the examination region 114. It will be appreciated that such radiation 120 can be emitted substantially continuously and/or can be emitted intermittently (e.g., a brief pulse of radiation is emitted followed by a resting period during which the radiation source 118 is not activated).

As the emitted radiation 120 traverses the object(s) 102, the radiation 120 can be attenuated differently by different aspects of the object(s) 102. Because different aspects attenuate different percentages of the radiation 120, an image(s) can be generated based upon the attenuation, or variations in the number of photons that are detected by the detector array 106. For example, more dense aspects of the object(s) 102, such as a bone or metal plate, can attenuate more of the radiation 120 (e.g., causing fewer photons to strike the detector array 106) than less dense aspects, such as skin or clothing.

The detector array 106 can comprise a linear (e.g., one-dimensional) or two-dimensional array of pixels (sometimes referred to as cells or elements) disposed as a single row or multiple rows in the shape of spherical arc, typically having a center of curvature at the focal spot of the radiation source(s) 118, for example. As the rotating structure 104 rotates, the detector array 106 is configured to directly convert (e.g., using amorphous selenium and/or other direct conversion materials) and/or indirectly convert (e.g., using Cesium Iodide (CsI) and/or other indirect conversion materials) detected radiation into electrical signals.

Signals that are produced by the detector array 106 can be transmitted to a data acquisition component 122 that is in operable communication with the detector array 106. Typically, the data acquisition component 122 is configured to convert the electrical signals output by the detector array 106 into digital data and/or to combine the digital data acquired during a measuring interval. The collection of digital output signals for a measuring interval can be referred to as a "projection" or a "view".

The example environment 100 also illustrates an image reconstructor 124 that is operably coupled to the data acquisition component 122 and is configured to generate one or more images representative of the object 102 under examination based at least in part upon signals output from the data acquisition component 122 using suitable analytical, iterative, and/or other reconstruction technique (e.g., tomosynthesis reconstruction, back-projection, iterative reconstruction, etc.).

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input, which can direct operations of the examination unit 108 (e.g., a speed of rotation for the rotating structure 104, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

It will be appreciated that the example component diagram is merely intended to illustrate one embodiment of one type of imaging modality and is not intended to be interpreted in a limiting manner. For example, the functions of one or more components described herein can be separated into a plurality of components and/or the functions of two or more components described herein can be consolidated into merely a single component. Moreover, the imaging modality can comprise additional components to perform additional features, functions, etc. (e.g., such as automatic threat detection).

Figure 2:
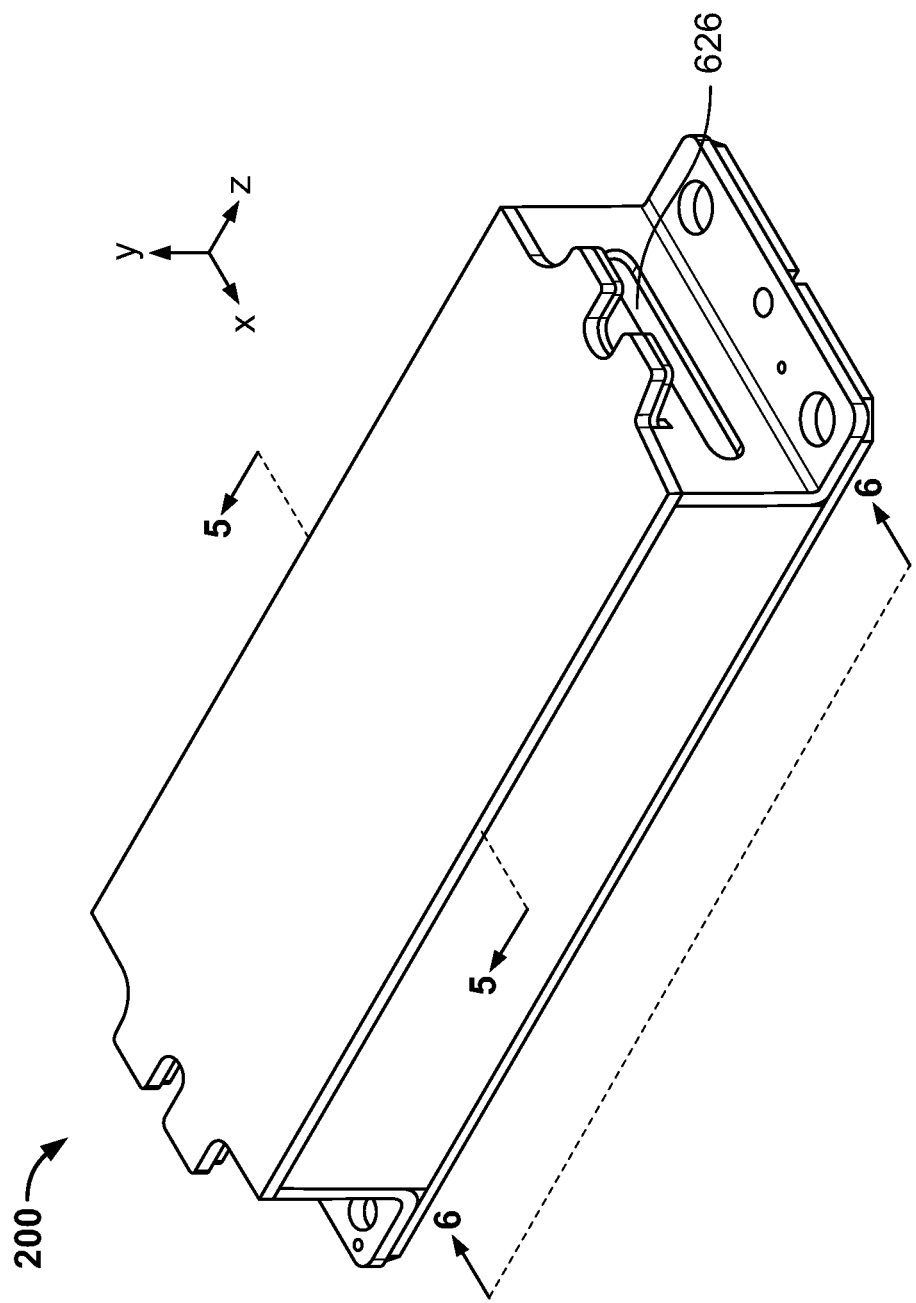
FIG. 2 illustrates an example anti-scatter collimator.

FIG. 2 illustrates an example anti-scatter collimator 200. The anti-scatter collimator 200 can be disposed between the radiation source 118 and the detector array 106. In some embodiments, the anti-scatter collimator 200 is a pre-object (also referred to as a pre-patient) anti-scatter collimator disposed between the radiation source 118 and the object 102 (e.g., such as at a base of the radiation source 118). In other embodiments, the anti-scatter collimator 200 is a post-object (also referred to as a post-patient) anti-scatter collimator disposed between the object 102 and the detector array 106. For example, in some embodiments, the anti-scatter collimator 200 is mounted to an upper surface of the detector array 106 that faces the radiation source 118, although other. The anti-scatter collimator 200 is configured to absorb, or otherwise alter secondary radiation, such that it is not detected by channels of the detector array 106, while allowing primary radiation to pass through (e.g., along the y-direction).

Figure 3:
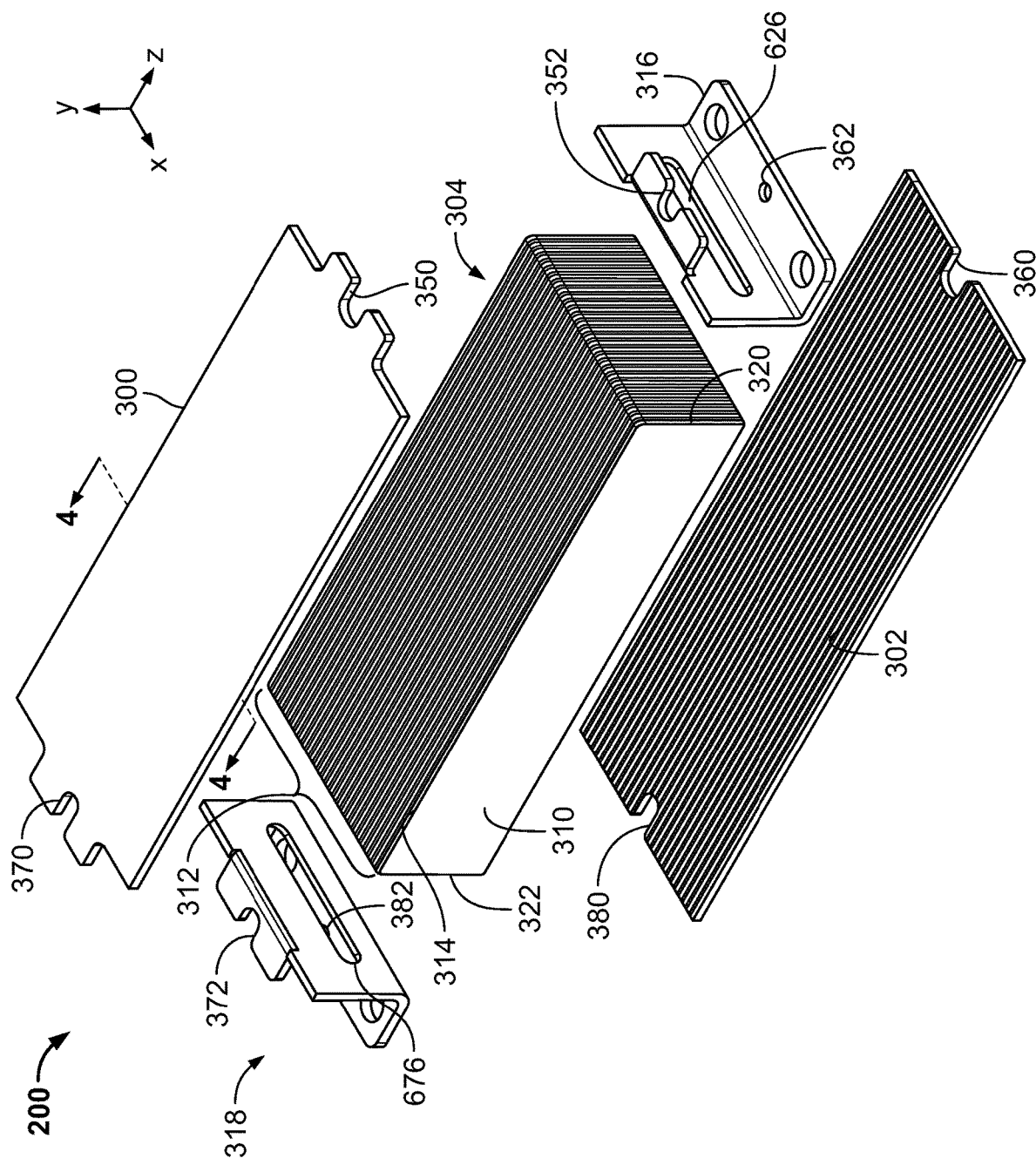
FIG. 3 illustrates an exploded view of an example anti-scatter collimator.

Referring to FIG. 3, an exploded view of the anti-scatter collimator 200 is illustrated. The anti-scatter collimator 200 comprises a first layer 300 and a second layer 302. The first layer 300 and the second layer 302 can extend substantially parallel to one another, and can be positioned to extend substantially perpendicular to a direction along which the radiation impinges upon the anti-scatter collimator 200 (e.g., along the y-direction). The first layer 300 can have a first attenuation coefficient. The second layer 302 can have a second attenuation coefficient. In an example, the first attenuation coefficient can be equal to the second attenuation coefficient, such that primary radiation can pass through the first layer 300 and the second layer 302 without being attenuated, absorbed, etc.

In an example, the first layer 300 and/or the second layer 302 may comprise a carbon fiber material with a thickness that is between about 0.5 millimeters (mm) to about 1.5 mm, or between about 0.75 mm to about 1.25 mm, or about 1 mm, although other materials and/or thicknesses are contemplated. The material and thickness of the first layer 300 and the second layer are typically selected to minimized radiation attenuation. For example, the material and thickness of first layer 300 and/or the second layer 302 may be selected to attenuate less than about 1% to 3% per layer. As such, a total combined attenuation for the first layer 300 and the second layer 302 may be between about 2% to about 6%, or even less. At a range of about 50 kiloelectron-Volts (keV) to about 160 keV, the first layer 300 can have a first attenuation coefficient and/or the second layer 302 can have a second attenuation coefficient that are between about 0.2 centimeters $(cm)^{-1}$ to about 0.3 $cm^{-1}$.

The anti-scatter collimator 200 comprises a plurality of anti-scatter plates, or a set 304 of septa. The set 304 of septa are configured to absorb, attenuate, or otherwise alter secondary radiation so that it is not detected by the channels of the detector array. The set 304 of septa can comprise, for example, molybdenum, tungsten, and/or any other material that has characteristics that allow for absorption or otherwise alteration of radiation striking the set 304 of septa.

In an example, a septum 310 and a plurality of other septa 312 can together define the set 304 of septa. The set 304 of septa can be disposed between the first layer 300 and the second layer 302. In an example, the septa can have a third attenuation coefficient that is greater than the first attenuation coefficient and the second attenuation coefficient. The first attenuation coefficient and the second attenuation coefficient are such that primary radiation and secondary radiation can pass through the first layer 300 and the second layer 302. The third attenuation coefficient is such that radiation impinging upon a septum of the set 304 is absorbed and/or attenuated.

In an example, the septa 312 may comprise a tungsten material (e.g., tungsten epoxy) with a thickness that is between about 50 micrometers (μμl) to about 150 μm, or between about 75 μm to about 125 μm, or about 100 μm. In an example, at about 50 keV to about 160 keV, the septa 312 can have an attenuation coefficient that is between about 50 $cm^{-1}$ to about 150 $cm^{-1}$, or between about 75 $cm^{-1}$ to about 125 $cm^{-1}$, or about 100 $cm^{-1}$. In addition or in the alternative to the tungsten material, the septa 312 may comprise other materials such as one or more of molybdenum, gold, thallium, lead, etc.

The septa 310, 312 are spaced apart to define transmission channels 314 (e.g., also illustrated in FIG. 4A) between adjacent septa 310, 312. In an example, the transmission channels 314 are configured to allow primary radiation to pass through the anti-scatter collimator 200 (e.g., along the y-direction), whereupon the primary radiation can be detected by the underlying detector array 106. In this way, primary radiation can pass through the anti-scatter collimator 200 while the secondary radiation is absorbed and/or attenuated by the septa 310, 312. As such, the secondary radiation is not detected by the underlying detector array 106.

The anti-scatter collimator 200 comprises one or more end supports for supporting the set 304 of septa, such as an end support 316 and a second end support 318. The end support 316 can be attached to the first layer 300 and the second layer 302. The end support 316 can be attached to the first layer 300 and the second layer 302 in a number of ways, such as with mechanical fasteners (e.g., bolts, screws, etc.), adhesives, etc. By being attached to the first layer 300 and the second layer 302, the end support 316 can maintain the relative positions of the first layer 300 and the second layer 302. The end support 316 and the second end support 318 may comprise, for example, a substantially rigid material such as a metals, plastics, etc.

The second end support 318 can be attached to the first layer 300 and the second layer 302 in a number of ways, such as with mechanical fasteners (e.g., bolts, screws, etc.), adhesives, etc. By being attached to the first layer 300 and the second layer 302, the second end support 318 can maintain the relative positions of the first layer 300 and the second layer 302. For example, the end support 316 and the second end support 318 can hold the first layer 300 and the second layer 302 at a fixed distance from each other, and limit inadvertent movement of the first layer 300 and the second layer 302.

In an example, the end support 316 can border an end 320 of the set 304 of septa, while the second end support 318 can border a second end 322 of the set 304 of septa. In this way, the set 304 of septa can be positioned between the end support 316 and the second end support 318. As such, the end support 316 and the second end support 318 can maintain a relative position of the set 304 of septa with respect to the end supports 316, 318.

The first layer 300 can be attached to the end support 316 in any number of ways. In an example, the first layer 300 defines a first layer opening 350 at an end of the first layer 300. The end support 316 defines a first support opening 352. In an example, the first layer opening 350 of the first layer 300 can be aligned with the first support opening 352 of the end support 316. In this way, a fastener can be received through the first layer opening 350 and the first support opening 352 to attach the first layer 300 and the end support 316. Moreover, this first layer opening 350 and the first support opening 352 can be used to ensure alignment of the end support 316 and the first layer.

The second layer 302 can be attached to the end support 316 in any number of ways. In an example, the second layer 302 defines a second layer opening 360 at an end of the second layer 302. The end support 316 defines a second support opening 362. In an example, the second layer opening 360 of the second layer 302 can be aligned with the second support opening 362 of the end support 316. In this way, a fastener can be received through the second layer opening 360 and the second support opening 362 to attach the second layer 302 and the end support 316. Moreover, this second layer opening 360 and the second support opening 362 can be used to ensure alignment of the end support 316 and the second layer.

The first layer 300 can be attached to the second end support 318 in any number of ways. In an example, the first layer 300 defines a third layer opening 370 at an end of the first layer 300. The second end support 318 defines a third support opening 372. In an example, the third layer opening 370 of the first layer 300 can be aligned with the third support opening 372 of the second end support 318. In this way, a fastener can be received through the third layer opening 370 and the third support opening 372 to attach the first layer 300 and the second end support 318. Moreover, this third layer opening 370 and the third support opening 372 can be used to further ensure alignment of the end support 316 and the first layer.

The second layer 302 can be attached to the second end support 318 in any number of ways. In an example, the second layer 302 defines a fourth layer opening 380 at an end of the second layer 302. The second end support 318 defines a fourth support opening 382. In an example, the fourth layer opening 380 of the second layer 302 can be aligned with the fourth support opening 382 of the second end support 318. In this way, a fastener can be received through the fourth layer opening 380 and the fourth support opening 382 to attach the second layer 302 and the second end support 318. Moreover, this fourth layer opening 380 and the third support opening 372 can be used to further ensure alignment of the end support 316 and the first layer.

Figure 4A:
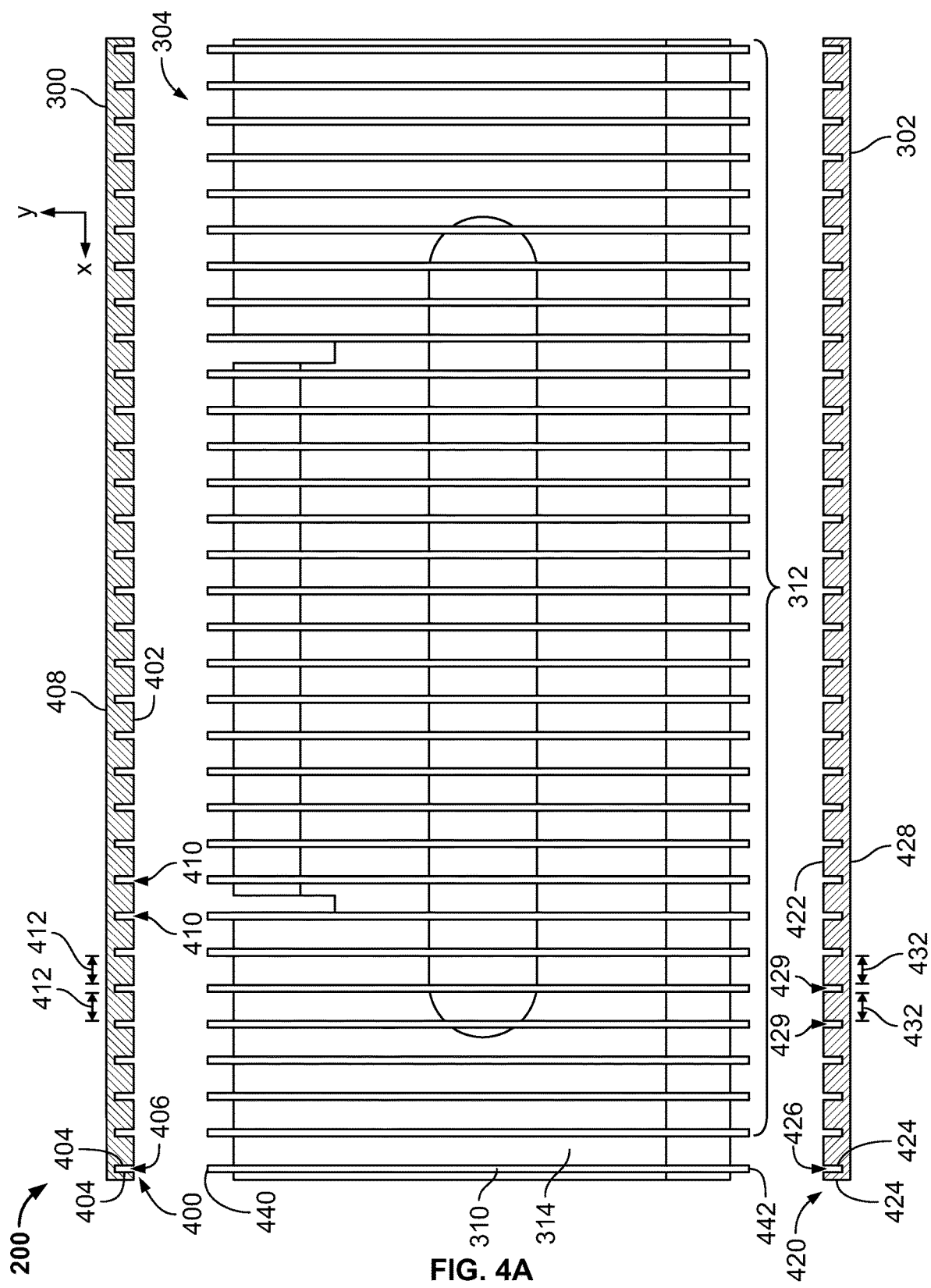
FIG. 4A illustrates an exploded sectional view of an example anti-scatter collimator in which septa are not attached to a first layer or a second layer and extend parallel to one another.

Referring to FIG. 4A, an exploded sectional view of the anti-scatter collimator 200 along lines 4-4 of FIG. 3 is illustrated. The first layer 300 defines one or more retaining members at a first surface 402. For example, the first layer 300 can define a first retaining member 400 at the first surface 402. In an example, the first surface 402 faces toward the septum 310 and the second layer 302.

The first retaining member 400 comprises a pair of first sidewalls 404 of the first layer 300. The first sidewalls 404 can define a first groove 406. The first groove 406 can therefore be defined in the first layer 300 and extend from the first surface 402 toward a second surface 408 that is opposite the first surface 402 of the first layer 300. A plurality of first grooves 410 can be defined in the first surface 402 of the first layer 300. The first grooves 410 can extend substantially parallel to each other. In an example, a pitch 412 at the first surface 402 between each first groove can be substantially constant. In another example, the pitch 412 at the first surface 402 between each first groove can be non-constant and/or different.

The second layer 302 defines one or more second retaining members at a first surface 422. For example, the second layer 302 can define a second retaining member 420 at the first surface 422. In an example, the first surface 422 faces toward the septa 310, 312 and the first layer 300.

The second retaining member 420 comprises a pair of second sidewalls 424 of the second layer 302. The second sidewalls 424 can define a second groove 426. The second groove 426 can therefore be defined in the second layer 302 and extend from the first surface 422 toward a second surface 428 that is opposite the first surface 422 of the second layer 302. A plurality of second grooves 429 can be defined in the first surface 422 of the second layer 302. The second grooves can extend substantially parallel to each other and to the first grooves. In an example, a pitch 432 at the first surface 422 between each second groove can be substantially constant. In another example, the pitch 432 at the first surface 402 between each second groove can be non-constant and/or different.

The septa 310, 312 can be disposed between the first layer 300 and the second layer 302. In an example, the septa 310, 312 can extend substantially perpendicular to the first layer 300 and the second layer 302. The septa 310, 312 can have a third attenuation coefficient that is greater than the first attenuation coefficient of the first layer 300 and the second attenuation coefficient of the second layer 302. In an example, a first end 440 of the septa 310, 312 can be positioned in proximity to the first layer 300 while a second end 442 can be positioned in proximity to the second layer 302. In an example, the first end 440 of the septa 310, 312 can be received within the first groove 406 such that the first end 440 is positioned between the first surface 402 of the first layer 300 and the second surface 408 of the first layer 300. In an example, the second end 442 of the septa 310, 312 can be received within the second groove 426 such that the second end 442 is positioned between the first surface 422 of the second layer 302 and the second surface 428 of the second layer 302.

Figure 4B:
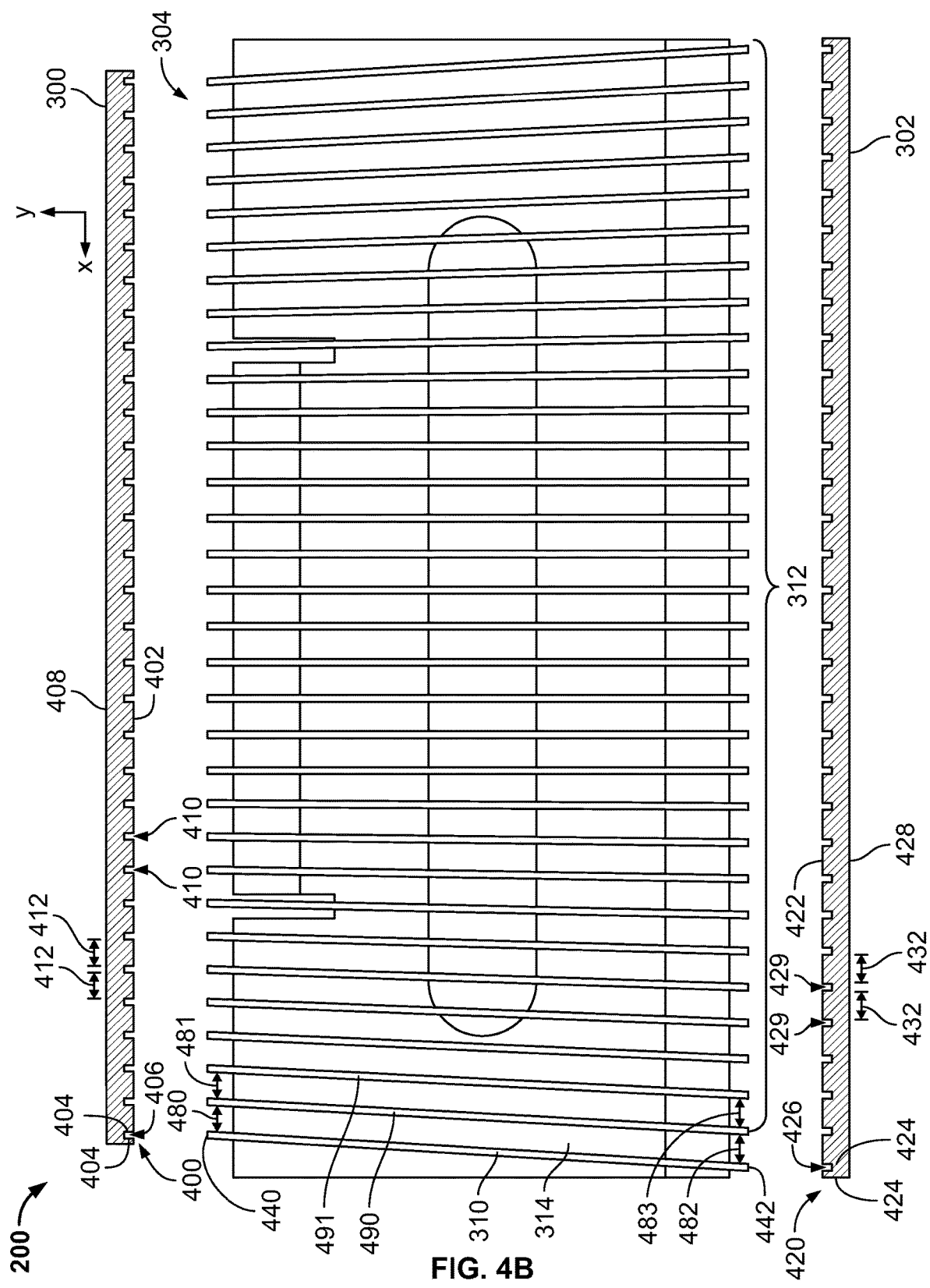
FIG. 4B illustrates an exploded sectional view of an example anti-scatter collimator in which septa are not attached to a first layer or a second layer and extend non-parallel to one another.

Referring to FIG. 4B, an exploded sectional view of another example of the anti-scatter collimator 200 is illustrated. In contrast to the septa 310, 312 of FIG. 4A that extend substantially parallel to one another, at least some of the septa 310, 312 of FIG. 4B can extend non-parallel to one another. In this way, the septa 310, 312 of FIG. 4B can converge toward a common focal spot, such that the septa 310, 312 can be separated from one another by a non-constant pitch.

In an example, the septum 310 can be spaced apart from a second septum 490, while the second septum 490 can be spaced apart from a third septum 491. As such, the second septum 490 is positioned between the septum 310 and the third septum 491. A first pitch 480 can separate the septum 310 and the second septum 490 at the first surface 402 of the first layer 300. A second pitch 482 can separate the septum 310 and the second septum 490 at the first surface 422 of the second layer 302. In an example, the first pitch 480 between the septum 310 and the second septum 490 may be different than the second pitch 482 between the septum 310 and the second septum 490. For example, the first pitch 480 may be less than the second pitch 482. In this way, a pitch between the septum 310 and the second septum 490 at the first surface 402 of the first layer 300 or the first surface 422 of the second layer 302 may be non-constant when moving from an end (e.g., at 440 or 442) of the septa 310, 490 toward the center of the septa 310, 490. For example, the pitch between the septum 310 and the second septum 490 can decrease when moving from the first surface 422 of the second layer 302 toward the first surface 402 of the first layer 300.

In an example, a third pitch 481 can separate the second septum 490 and the third septum 491 at the first surface 402 of the first layer 300. A fourth pitch 483 can separate the second septum 490 and the third septum 491 at the first surface 422 of the second layer 302. In an example, the third pitch 481 between the second septum 490 and the third septum 491 may be different than the fourth pitch 483 between the second septum 490 and the third septum 491. For example, the third pitch 481 may be less than the fourth pitch 483. In this way, a pitch between the second septum 490 and the third septum 491 at the first surface 402 of the first layer 300 or the first surface 422 of the second layer 302 may be non-constant when moving from an end of the septa 490, 491 toward the center of the septa 490, 491. For example, the pitch between the second septum 490 and the third septum 491 can decrease when moving from the first surface 422 of the second layer 302 toward the first surface 402 of the first layer 300.

In an example, a pitch at one of the first surface 402 of the first layer 300 or the first surface 422 of the second layer 302 between each septum of the set 304 of septa may be substantially constant. For example, the pitch between each septum of the set 304 of septa at the first surface 422 of the second layer 302 may be substantially constant. However, the pitch between each septum of the set 304 of septa at the first surface 402 of the first layer 300 may be non-constant. In such an example, the pitch at the first surface 402 of the first layer 300 between outer septa (e.g., toward the left and right sides of FIG. 4B) may be less than the pitch between center septa (e.g., toward the center of FIG. 4B). For example, the second pitch 482 and the fourth pitch 483 may be substantially the same, while the first pitch 480 may be less than the third pitch 481 (and also less than the second pitch 482 and the fourth pitch 483).

Figure 5:
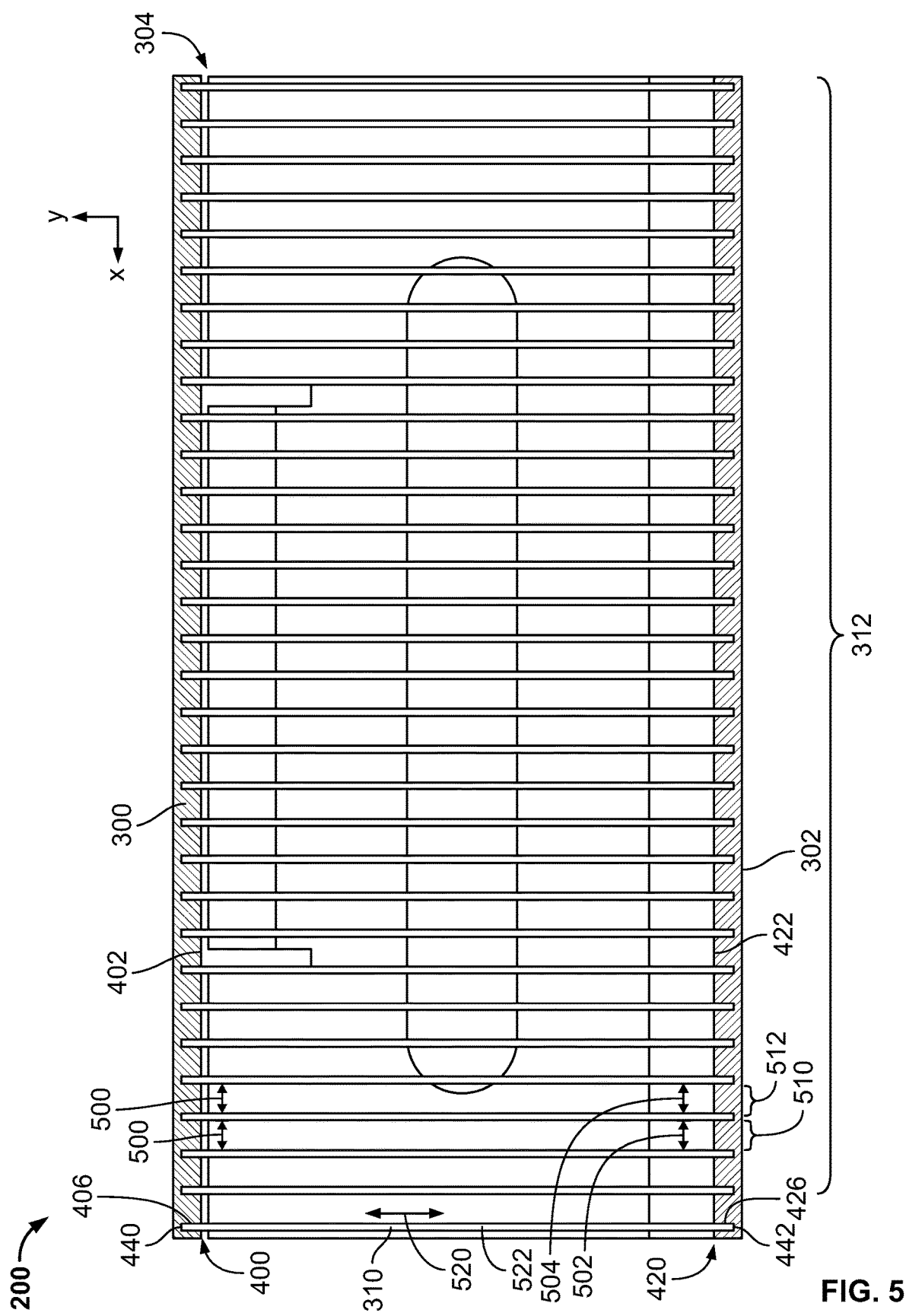
FIG. 5 illustrates a sectional view of an example anti-scatter collimator in which septa are attached to a first layer or a second layer.

Referring to FIG. 5, a sectional view of the anti-scatter collimator 200 of FIG. 4A along lines 5-5 of FIG. 2 is illustrated. In an example, the septa 310, 312 can be maintained in place relative to the first layer 300 and the second layer 302 by physically contacting the first retaining member 400 and the second retaining member 420. For example, the septum 310 can be received within the first groove 406 and the second groove 426. In an example, the first end 440 of the septum 310 can be received within the first groove 406 while the second end 442 of the septum 310 can be received within the second groove 426. In this way, the first retaining member 400 and the second retaining member 420 can maintain the position of the septum 310 relative to the first layer 300 and the second layer 302.

In an example, a pitch 500 at the first surface 402 of the first layer 300 between each septa 310, 312 of the set 304 of septa can be substantially constant. In an example, a second and third pitch 502, 504 at the first surface 422 of the second layer 302 between a first subset 510 of septa and a second subset 512 of septa can be different. For example, a second pitch 502 can be defined between the first subset 510 of septa. A third pitch 504 can be defined between the second subset 512 of septa. In an example, the second pitch 502 can be different than the third pitch 504. For example, the second pitch 502 can be larger than the third pitch 504. In this way, the second and third pitch 502, 504 between the septa 310, 312 at the first surface 422 of the second layer 302 can be non-constant while the pitch 500 between the septa 310, 312 at the first surface 402 of the first layer 300 can be constant.

In an example, the set 304 of septa can be stacked in a first direction 520 to define a stack having an end (e.g., the first end 440 and the second end 442) and a center 522. The first and second ends 440, 442 can be in contact with the first retaining member 400 and the second retaining member 420, while the center 522 is positioned between the first retaining member 400 and the second retaining member 420. In an example, a pitch between the septa 310, 312 at the second layer 302 (e.g., the second pitch 502, the third pitch 504, etc.) is non-constant (e.g., can decrease) moving from the second end 442 toward the center 522. In this way, in an example, the pitch between adjacent septa can be non-constant when moving from one end (e.g., the second end 442, for example) to another end (e.g., the first end 440, for example).

Figure 6:
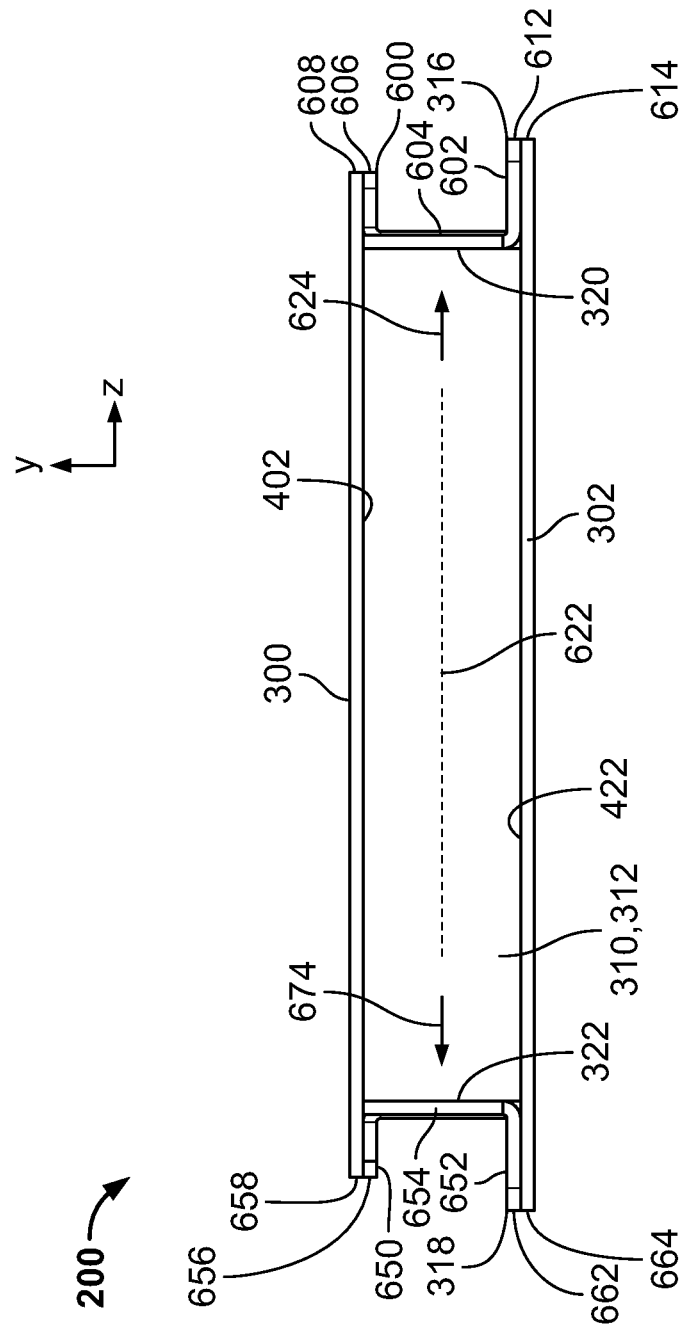
FIG. 6 illustrates an example anti-scatter collimator in which end supports are attached to a first layer and a second layer.

Referring to FIG. 6, a side view of the anti-scatter collimator 200 along lines 6 6 of FIG. 2 is illustrated. In an example, the end support 316 and the second end support 318 can be attached to the first layer 300 and to the second layer 302. The end support 316 comprises a first support portion 600, a second support portion 602, and a third support portion 604. The first support portion 600 can be attached to the first layer 300. In an example, the first support portion 600 extends substantially parallel to the first surface 402 of the first layer 300. The first support portion 600 can extend adjacent to and/or in contact with the first surface 402. In an example, a first support end 606 of the first support portion 600 can be substantially flush and aligned with a first end 608 of the first layer 300.

In an example, the second support portion 602 of the end support 316 can be attached to the second layer 302. The second support portion 602 can extend substantially parallel to the first surface 422 of the second layer 302. The second support portion 602 can extend adjacent to and/or in contact with the first surface 422. In this way, the second support portion 602 can be spaced apart from and extend substantially parallel to the first support portion 600. In an example, a first support end 612 of the second support portion 602 can be substantially flush and aligned with a first end 614 of the second layer 302.

In an example, the third support portion 604 of the end support 316 can extend between the first support portion 600 and the second support portion 602. The third support portion 604 can extend substantially perpendicular to at least one of the first support portion 600 and the second support portion 602. The third support portion 604 can be attached to the first support portion 600 and the second support portion 602. In this way, the third support portion 604 can maintain a relative position of the first support portion 600 with respect to the second support portion 602, such as by positioning the first support portion 600, second support portion 602, and the third support portion 604 to form a channel-shaped end support 316, as shown in FIG. 6. The third support portion 604 can be attached to the first support portion 600 and the second support portion 602 in any number of ways, such as by being formed a single composite piece (e.g., as illustrated), by mechanical fasteners, adhesives or welding, etc.

The third support portion 604 can border the first longitudinal end 320 of the septa 310, 312. In an example, the third support portion 604 can extend substantially perpendicular to an axis 622 along which the septa 310, 312 extend. In this way, the third support portion 604 can limit movement of the septa 310, 312 along a first direction 624 that is substantially parallel to the axis 622. In an example, the third support portion 604 defines a window 626 (e.g., illustrated in FIGS. 2 and 3) through which the septa 310, 312 are visible.

The second end support 318 is similar in structure to the end support 316. In an example, the second end support 318 comprises a first support portion 650, a second support portion 652, and a third support portion 654. The first support portion 650 can be attached to the first layer 300. In an example, the first support portion 650 extends substantially parallel to the first surface 402 of the first layer 300. The first support portion 650 can extend adjacent to and/or in contact with the first surface 402. In an example, a second support end 656 of the first support portion 600 can be substantially flush and aligned with a second end 658 of the first layer 300. The first support portion 650 of the second end support 318 can extend substantially parallel to and co-planar with the first support portion 600 of the end support 316.

In an example, the second support portion 652 of the second end support 318 can be attached to the second layer 302. The second support portion 652 can extend substantially parallel to the first surface 422 of the second layer 302. The second support portion 652 can extend adjacent to and/or in contact with the first surface 422. In this way, the second support portion 652 can be spaced apart from and extend substantially parallel to the first support portion 650. In an example, a second support end 662 of the second support portion 652 can be substantially flush and aligned with a second end 664 of the second layer 302. The second support portion 652 of the second end support 318 can extend substantially parallel to and co-planar with the first support portion 650 of the second end support 318.

In an example, the third support portion 654 of the second end support 318 can extend between the first support portion 650 and the second support portion 652. The third support portion 654 can extend substantially perpendicular to at least one of the first support portion 650 and the second support portion 652. The third support portion 654 can be attached to the first support portion 650 and the second support portion 652. In this way, the third support portion 654 can maintain a relative position of the first support portion 650 with respect to the second support portion 652. The third support portion 654 can be attached to the first support portion 650 and the second support portion 652 in any number of ways, such as by being formed a single composite piece (e.g., as illustrated), by mechanical fasteners, adhesives or welding, etc. In an example, the third support portion 654 of the second end support 318 can extend substantially parallel to the third support portion 604 of the end support 316.

The third support portion 654 can border the second longitudinal end 322 of the septa 310, 312. In an example, the third support portion 654 can extend substantially perpendicular to the axis 622 along which the septa 310, 312 extend. In this way, the third support portion 654 can limit movement of the septa 310, 312 along a second direction 674 that is substantially parallel to the axis 622. In an example, the third support portion 654 defines a window 676 (e.g., illustrated in FIGS. 2 and 3) through which the septa 310, 312 are visible.

Figure 7:
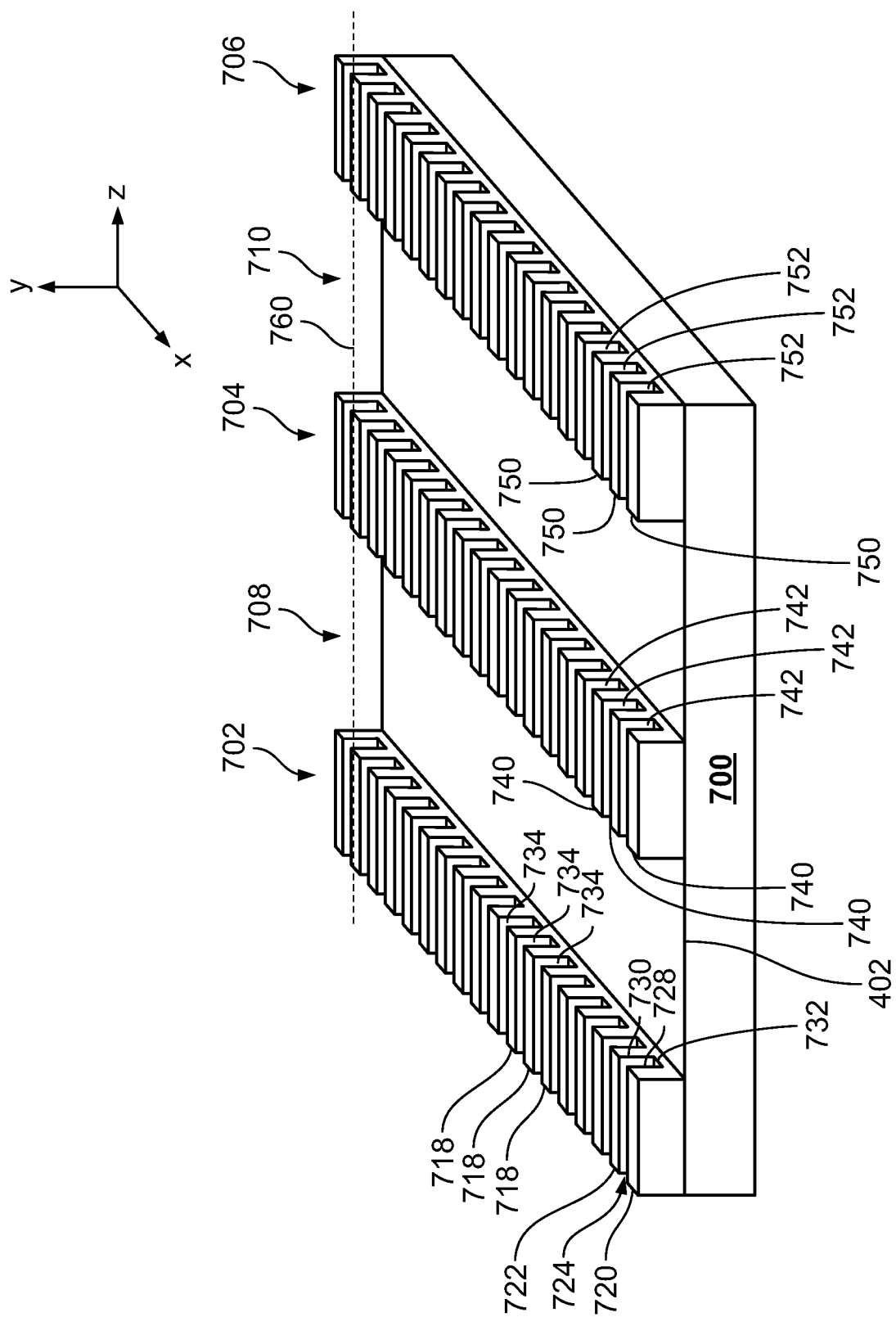
FIG. 7 illustrates an example anti-scatter collimator comprising a retaining member.

Referring to FIG. 7, a second example of a first layer 700 is illustrated. The second layer can be substantially similar to the first layer 700 illustrated in FIG. 7, or, can be substantially similar to the second layer 302 illustrated in FIGS. 2 to 6. The first layer 700 comprises a first retaining member 702, a second retaining member 704, and a third retaining member 706. The second retaining member 704 can be spaced apart from and disposed between the first retaining member 702 and the third retaining member 706. In this way, an opening 708 can be defined between the first retaining member 702 and the second retaining member 704, while a second opening 710 can be defined between the second retaining member 704 and the third retaining member 706.

The first retaining member 702 comprises a plurality of protruding members 718, including a first protruding member 720 and a second protruding member 722. The first protruding member 720 and the second protruding member 722 extend from the first surface 402 of the first layer 700 toward the first surface 422 of the second layer 302. In an example, the first protruding member 720 and the second protruding member 722 can be spaced apart such that a groove 724 is defined by the protruding members. For example, the groove 724 can be defined between the first protruding member 720 and the second protruding member 722. In an example, the groove 724 can be defined by a first sidewall 728 of the first protruding member 720, a second sidewall 730 of the second protruding member 722, and a bottom surface 732. In an example, the first surface 402 of the first layer 700 comprises the bottom surface 732. In another example, the bottom surface 732 can be defined along a third protruding member that protrudes from the first surface 402 and extends between the first protruding member 720 and the second protruding member 722. In such an example, the groove 724 can be defined by the first sidewall 728 of the first protruding member 720, the second sidewall 730 of the second protruding member 722, and the bottom surface 732 of the third protruding member.

Additional grooves 734 can be defined between the adjacent protruding members 718 of the first retaining member 702. The grooves 734 can be similar to the groove 724 defined by the first protruding member 720 and the second protruding member 722. In an example, the second retaining member 704 is similar in structure to the first retaining member 702. For example, the second retaining member 704 comprises a plurality of protruding members 740 that extend from the first surface 402 of the first layer 700 toward the first surface 422 of the second layer 302. The protruding members 740 can be spaced apart to define second grooves 742 between adjacent protruding members 740. In an example, the third retaining member 706 is similar in structure to the first retaining member 702 and the second retaining member 704. For example, the third retaining member 706 comprises a plurality of protruding members 750 that extend from the first surface 402 of the first layer 700 toward the first surface 422 of the second layer 302. The protruding members 750 can be spaced apart to define third grooves 752 between adjacent protruding members 750.

The grooves 724, 734, 742, 752 of the first retaining member 702, the second retaining member 704, and the third retaining member 706 can be axially aligned. For example, an axis 760 can intersect one of the grooves 734 of the first retaining member 702, one of the second grooves 742 of the second retaining member 704, and one of the third grooves 752 of the third retaining member 706. The remaining grooves 734, 742, 752 can similarly be aligned with the axis 760 so as to extend substantially parallel to the axis 760. In this way, the grooves 734, 742, 752 can receive the septa 310, 312 so as to maintain the septa 310, 312 relative to the first layer 700.

Figure 8:
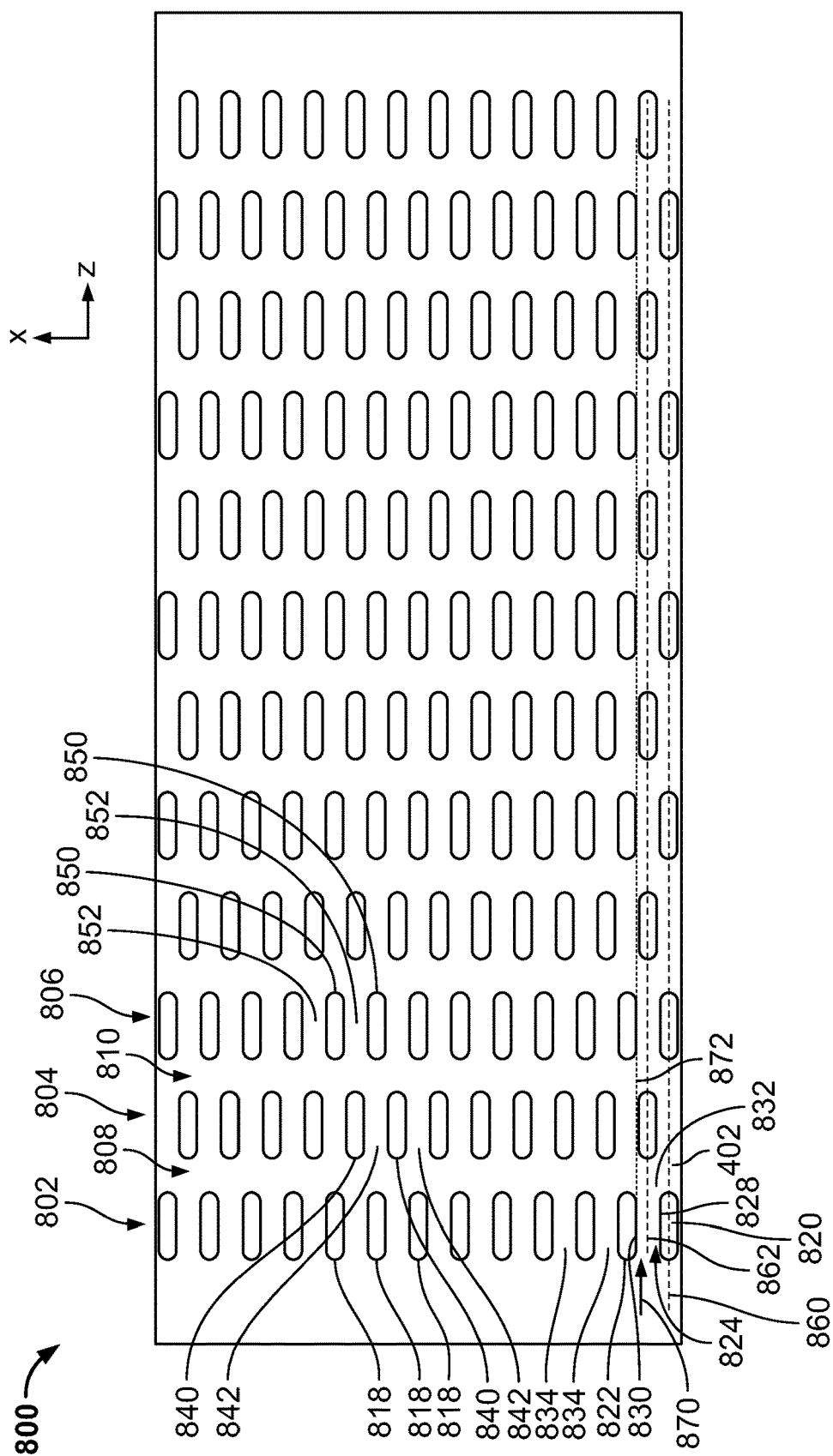
FIG. 8 illustrates an example anti-scatter collimator comprising a retaining member.
Figure 9:
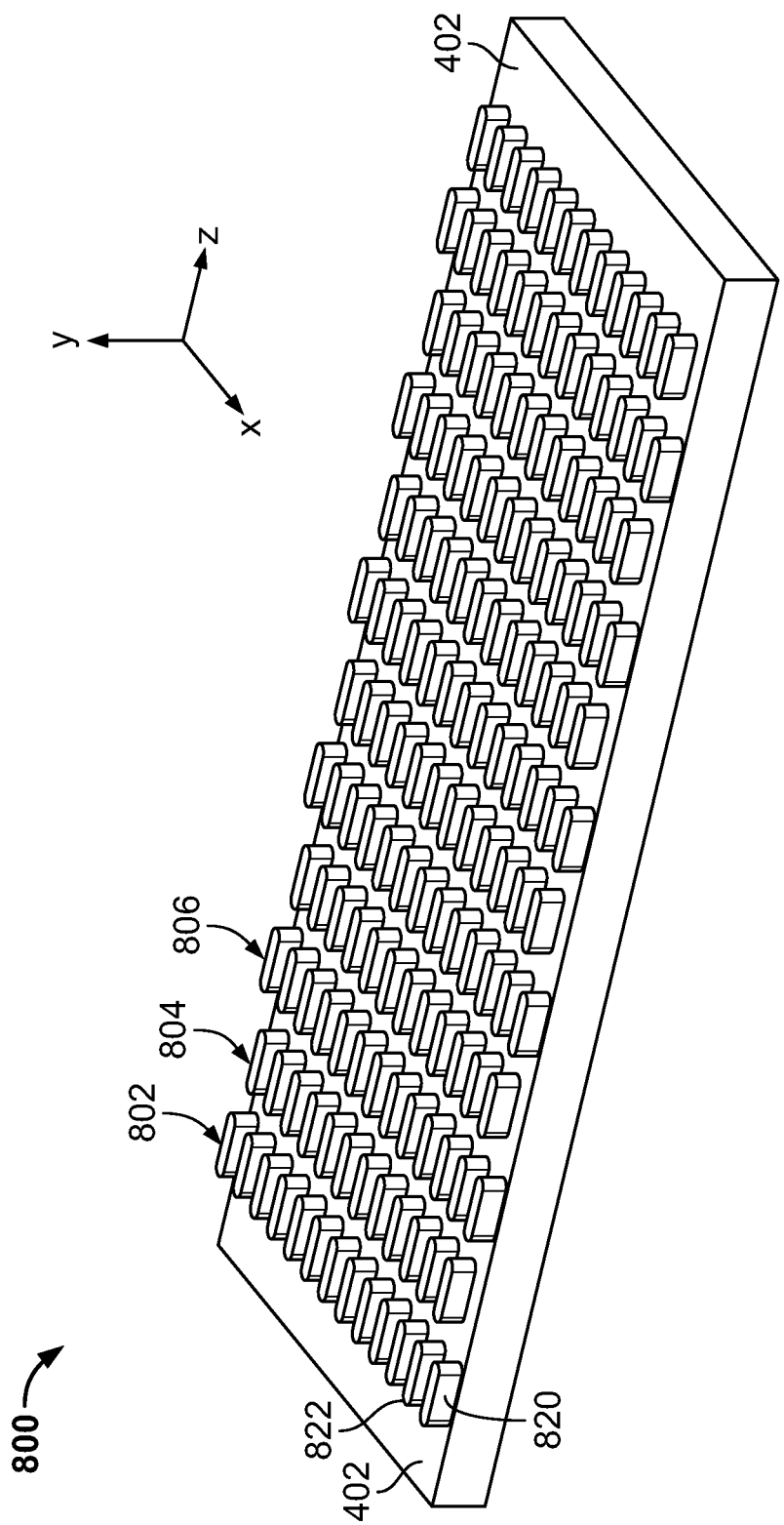
FIG. 9 illustrates an example anti-scatter collimator comprising a retaining member.

Referring to FIGS. 8 and 9, a third example of a first layer 800 is illustrated. The second layer can be similar to the first layer 800 in FIG. 8, the first layer 700 illustrated in FIG. 7, or the second layer 302 illustrated in FIGS. 2 to 6. The first layer 800 comprises one or more retaining members, such as a first retaining member 802, a second retaining member 804, a third retaining member 806, etc. The second retaining member 804 can be spaced apart from and disposed between the first retaining member 802 and the third retaining member 806. In this way, an opening 808 can be defined between the first retaining member 802 and the second retaining member 804, while a second opening 810 can be defined between the second retaining member 804 and the third retaining member 806.

The first retaining member 802 comprises a plurality of protruding member 818, including a first protruding member 820 and a second protruding member 822. The first protruding member 820 and the second protruding member 822 extend from the first surface 402 of the first layer 800 toward the first surface 422 of the second layer 302.

In an example, the first protruding member 820 and the second protruding member 822 can be spaced apart such that a groove 824 is defined by the protruding members. For example, the groove 824 can be defined between the first protruding member 820 and the second protruding member 822. In an example, the groove 824 can be defined by a first sidewall 828 of the first protruding member 820, a second sidewall 830 of the second protruding member 822, and a bottom surface 832. In an example, the first surface 402 of the first layer 800 comprises the bottom surface 832. In another example, the bottom surface 832 can be defined along a third protruding member that protrudes from the first surface 402 and extends between the first protruding member 820 and the second protruding member 822. Additional grooves 834 can be defined between the adjacent protruding members 818 of the first retaining member 802. The grooves 834 can be similar to the groove 824 defined by the first protruding member 820 and the second protruding member 822.

In an example, the second retaining member 804 is similar in structure to the first retaining member 802. For example, the second retaining member 804 comprises a plurality of protruding members 840 that extend from the first surface 402 of the first layer 800 toward the first surface 422 of the second layer 302. The protruding members 840 can be spaced apart to define second grooves 842 between adjacent protruding members 840. In an example, the third retaining member 806 is similar in structure to the first retaining member 802 and the second retaining member 804. For example, the third retaining member 806 comprises a plurality of protruding members 850 that extend from the first surface 402 of the first layer 800 toward the first surface 422 of the second layer 302. The protruding members 850 can be spaced apart to define third grooves 852 between adjacent protruding members 850.

In an example, protruding members of adjacent retaining members can be offset from each other. For example, the protruding members 818 of the first retaining members 802 can be offset from the protruding members 840 of the second retaining member 804. The protruding members 840 of the second retaining member 804 can be offset from the protruding members 850 of the third retaining member 806. However, the protruding members 818 of the first retaining members 802 can be aligned with the protruding members 850 of the third retaining member 806. In an example, by being aligned, an axis 860 can intersect the first protruding member 820 of the first retaining member 802 and one of the protruding members 850 of the third retaining member 806. In an example, by being offset, the axis 860 that intersects the first protruding member 820 of the first retaining member 802 and one of the protruding members 850 of the third retaining member 806 does not intersect the protruding members 840 of the second retaining member 804.

A second axis 862 can intersect one of the protruding members 840 of the second retaining member 804. In an example, the second axis 862 extends substantially parallel to the axis 860. Due to the first retaining member 802 being offset from the second retaining member 804, the second axis 862 does not intersect the first protruding member 820, the second protruding member 822, or the protruding members 818 of the first retaining member 802. Likewise, due to the third retaining member 806 being offset from the second retaining member 804, the second axis 862 does not intersect the protruding members 850 of the third retaining member 806.

A path 870 can be defined between the protruding members of the first retaining member 802, the second retaining member 804, and the third retaining member 806. In an example, the path 870 can extend along a path axis 872 that is substantially parallel to the axis 860 and the second axis 862. In an example, the path axis 872 does not intersect the protruding members 818, 820, 822 of the first retaining member 802, the protruding members 840 of the second retaining member 804, the protruding members 850 of the third retaining member 806, and at least some of the protruding members of the other retaining members. In an example, the path 870 can be defined between sidewalls of the protruding members of the retaining members. The path 870 can have a thickness that is greater than or equal to a thickness of the septa 310, 312. In this way, the septa 310, 312 can be received within the path 870, such that the retaining members 802, 804, 806 can maintain a position of the septa 310, 312 relative to the first layer 800.

It will be appreciated that the grooves described herein with respect to FIGS. 2 to 9 can be formed in any number of ways. In an example, some or all of the grooves (e.g., the grooves described with respect to FIGS. 2 to 6) can be formed by subtractive grooving techniques, such as dicing, saw cutting, laser cutting, water cutting, electrical discharge machining (EDM), etc. In an example, some or all of the grooves (e.g., the grooves described with respect to FIGS. 7 to 9) can be formed by additive grooving techniques, such as additive manufacturing (e.g., 3D printing), molding, etc.

Figure 10:
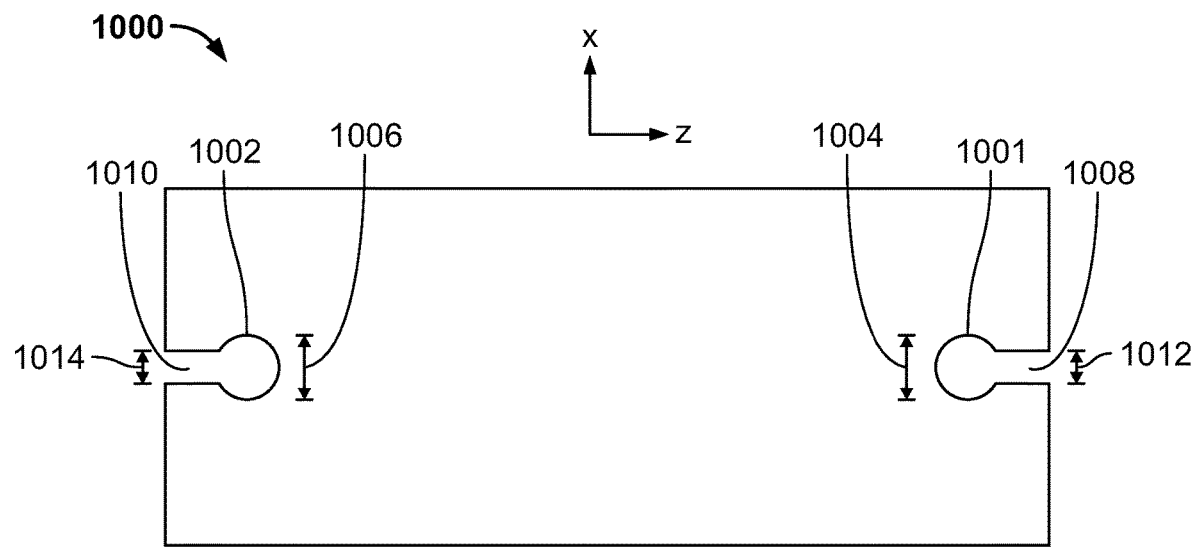
FIG. 10 illustrates an example first layer for an anti-scatter collimator.

Referring to FIG. 10, a fourth example of a first layer 1000 is illustrated. In an example, the first layer 1000 defines a first support opening 1001 and a third support opening 1002. The first layer 1000 can receive one or more fasteners through the first support opening 1001 and the third support opening 1002 to attach the first layer 1000 to the end support 316 and the second end support 318. In an example, the first support opening 1001 has a first cross-sectional size 1004, while the third support opening 1002 has a third cross-sectional size 1006. The first support opening 1001 and the third support opening 1002 have rounded shapes that can be partially, but not completely, surrounded by a wall of the first layer 1000.

The first support opening 1001 is defined adjacent to a first channel 1008. The first channel 1008 has a first channel cross-sectional size 1012. In an example, the first channel cross-sectional size 1012 is less than the first cross-sectional size 1004 of the first support opening 1001. The first layer 1000 is configured to receive a fastener through the first support opening 1001, wherein the fastener has a cross-sectional size that is smaller than the first cross-sectional size 1004 but larger than the first channel cross-sectional size 1012. In this way, the fastener is limited from being inadvertently removed from the first support opening 1001 through the first channel 1008.

The third support opening 1002 is defined adjacent to a third channel 1010. The third channel 1010 has a third channel cross-sectional size 1014. In an example, the third channel cross-sectional size 1014 is less than the third cross-sectional size 1006 of the third support opening 1002. The first layer 1000 is configured to receive a fastener through the third support opening 1002, wherein the fastener has a cross-sectional size that is smaller than the third cross-sectional size 1006 but larger than the third channel cross-sectional size 1014. In this way, the fastener is limited from being inadvertently removed from the third support opening 1002 through the third channel 1010.

Figure 11:
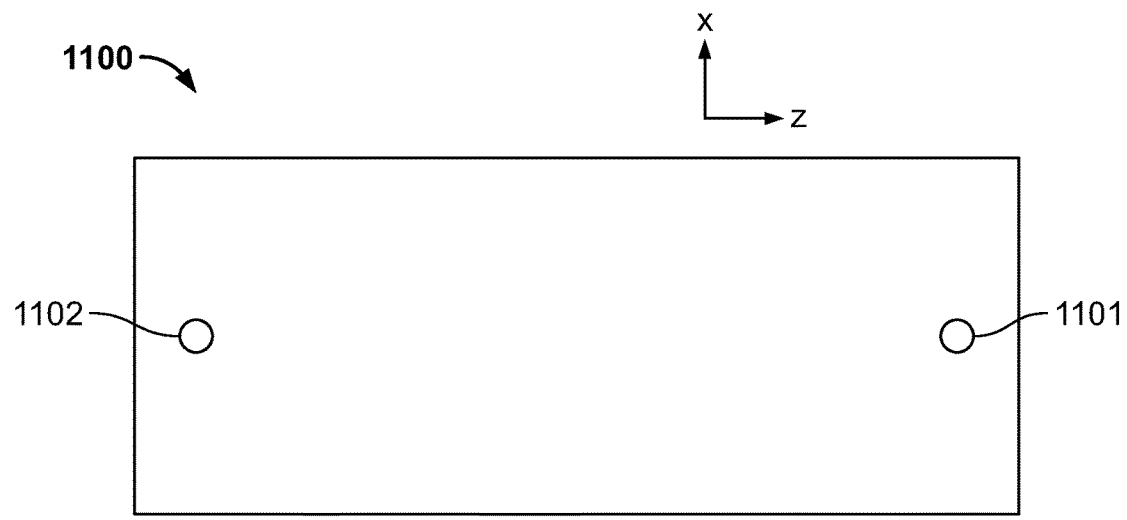
FIG. 11 illustrates an example first layer for an anti-scatter collimator.

Referring to FIG. 11, a fifth example of a first layer 1100 is illustrated. In an example, the first layer 1100 defines a first support opening 1101 and a third support opening 1102. The first layer 1100 can receive one or more fasteners through the first support opening 1101 and the third support opening 1102 to attach the first layer 1100 to the end support 316 and the second end support 318. In an example, the first support opening 1101 and the third support opening 1102 have substantially circular cross-sectional shapes, though other shapes are envisioned.

Figure 12:
FIG. 12 illustrates an example first layer for an anti-scatter collimator.

Referring to FIG. 12, a sixth example of a first layer 1200 is illustrated. In an example, the first layer 1200 comprises a first support opening 1201 and a third support opening 1202. The first layer 1200 can receive one or more fasteners through the first support opening 1201 and the third support opening 1202 to attach the first layer 1200 to the end support 316 and the second end support 318. In an example, the first support opening 1201 can have a non-circular shape, such as an oval shape, an elliptical shape, or a stadium shape (e.g., an oblong shape with two semicircles joined by straight lines). The third support opening 1202 can have a substantially circular cross-sectional shape, though other shapes are envisioned.

Figure 13:
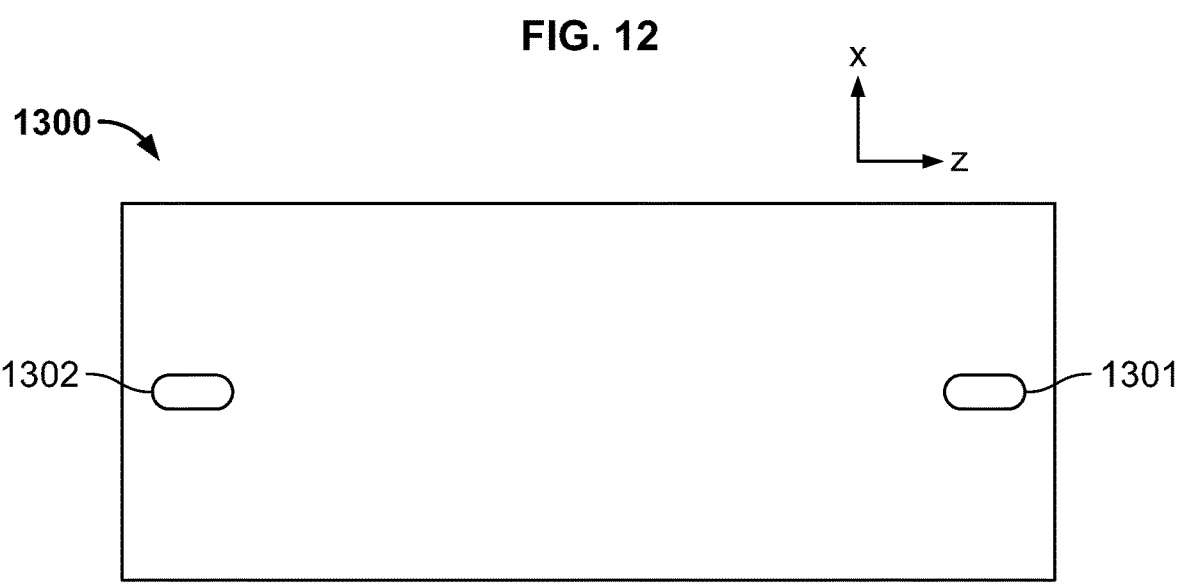
FIG. 13 illustrates an example first layer for an anti-scatter collimator.

Referring to FIG. 13, a seventh example of a first layer 1300 is illustrated. In an example, the first layer 1300 comprises a first support opening 1301 and a third support opening 1302. The first layer 1300 can receive one or more fasteners through the first support opening 1301 and the third support opening 1302 to attach the first layer 1300 to the end support 316 and the second end support 318. In an example, the first support opening 1301 and the third support opening 1302 can have a non-circular shape, such as an oval shape, an elliptical shape, or a stadium shape (e.g., an oblong shape with two semicircles joined by straight lines).

Figure 14:
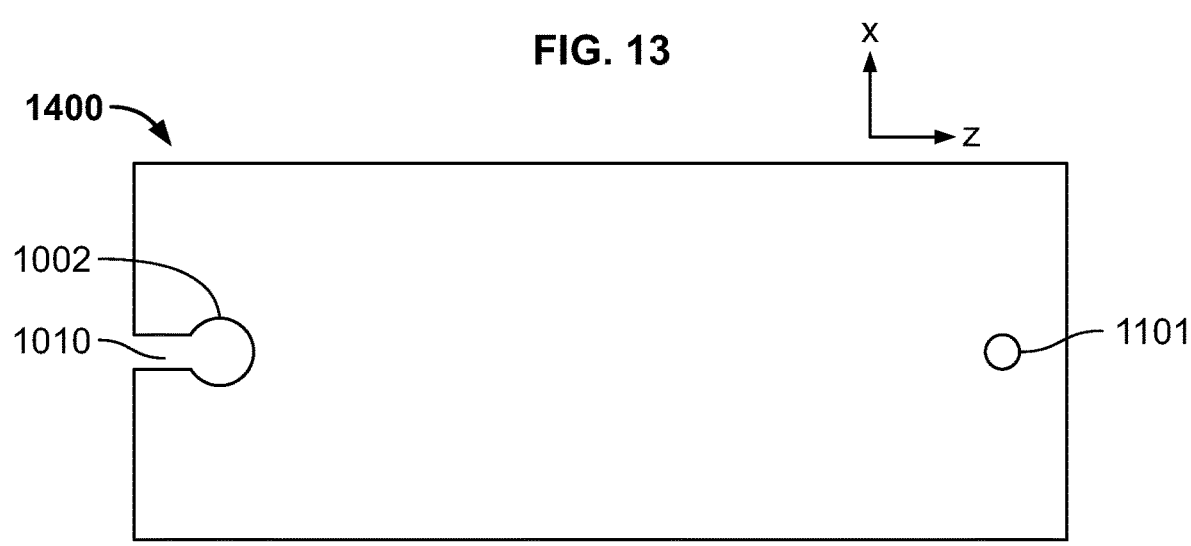
FIG. 14 illustrates an example first layer for an anti-scatter collimator.

Referring to FIG. 14, an eighth example of a first layer 1400 is illustrated. In an example, the first layer 1400 comprises the first support opening 1101, which has a substantially circular shape. The first layer 1400 can comprise the third support opening 1002 and the third channel 1010. The first layer 1400 can receive one or more fasteners through the first support opening 1101 and the third support opening 1002 to attach the first layer 1400 to the end support 316 and the second end support 318.

Despite relatively large inertial forces exerted upon the anti-scatter collimator 200 during operation, the septa may be maintained in place with reduced vibration and motion. For example, the first and second retaining members can contact the septum to maintain the position of the septum in place relative to the first layer and the second layer. The retaining members can be arranged to support the septum at least partially along the length of the septum. In this way, a first pair of opposing sides of the septum may be maintained in place with respect to the first layer and the second layer. A second pair of opposing sides of the septum may be maintained in place with respect to the end supports. Accordingly, unintended vibration, motion and/or misalignment of the septa are reduced during operation, thus allowing primary radiation to pass through the anti-scatter collimator 200 between the septa while the secondary radiation is absorbed and/or attenuated by the septa.

It can be appreciated that "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims can generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure can have been disclosed with respect to only one of several implementations, such feature can be combined with one or more other features of the other implementations as can be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An anti-scatter collimator, comprising:
    a first layer defining a first retaining member at a first surface of the first layer, wherein the first layer has a first attenuation coefficient;
    a second layer defining a second retaining member at a first surface of the second layer that faces the first surface of the first layer, wherein the second layer has a second attenuation coefficient;
    a septum disposed between the first layer and the second layer and physically contacting the first retaining member and the second retaining member, wherein:
        the first retaining member and the second retaining member maintain a position of the septum relative to the first layer and the second layer, and
        the septum has a third attenuation coefficient that is greater than the first attenuation coefficient and the second attenuation coefficient; and
    a channel-shaped end support with a first support portion of the end support attached to the first layer, a second support portion of the end support attached to the second layer, and a third support portion of the end support extending between the first support portion and the second support portion, the third support portion abutting against an end of the septum such that linear movement of the septum is constrained by the third support portion only within one plane.

2. The anti-scatter collimator of claim 1, wherein:
    a groove is defined in the first layer and extends from the first surface of the first layer toward a second surface of the first layer that is opposite the first surface of the first layer,
    the first retaining member comprises a pair of sidewalls of the first layer that define the groove, and
    the septum is disposed within the groove to maintain the position of the septum relative to the first layer.

3. The anti-scatter collimator of claim 1, wherein:
    the first retaining member comprises a protruding member that extends from the first surface of the first layer toward the first surface of the second layer,
    a groove is at least partially defined by the protruding member, and
    the septum is disposed within the groove to maintain the position of the septum relative to the first layer.

4. The anti-scatter collimator of claim 3, wherein the protruding member comprises a first protruding member, a second protruding member, and a third protruding member, the groove is defined by a first sidewall of the first protruding member, a second sidewall of the second protruding member, and a bottom surface of the third protruding member.

5. The anti-scatter collimator of claim 1, wherein:
    the first retaining member comprises a first protruding member that extends from the first surface of the first layer toward the first surface of the second layer and a second protruding member that extends from the first surface of the first layer toward the first surface of the second layer,
    a groove is defined between the first protruding member and the second protruding member, and
    the septum is disposed within the groove to maintain the position of the septum relative to the first layer.

6. The anti-scatter collimator of claim 5, wherein the groove is defined by a first sidewall of the first protruding member, a second sidewall of the second protruding member, and the first surface of the first layer.

7. The anti-scatter collimator of claim 1, further comprising
    a second channel-shaped end support comprising:
        a first support portion that is configured to be attached to the first layer;
        a second support portion that is configured to be attached to the second layer; and
        a third support portion that extends between the first support portion and the second support portion, the third support portion of the second end support abutting against a second end of the septum.

8. The anti-scatter collimator of claim 1, wherein:
    the first support portion extends substantially parallel to the first surface of the first layer,
    the first support portion defines a first support opening, and the first layer defines a first layer opening that aligns with the first support opening.

9. The anti-scatter collimator of claim 1, wherein the third support portion defines a window through which the septum is visible.

10. The anti-scatter collimator of claim 1, wherein the first attenuation coefficient is equal to the second attenuation coefficient.

11. The anti-scatter collimator of claim 1, wherein:
the septum and a plurality of other septa together define a set of septa, and
a pitch at one of the first surface of the first layer or the first surface of the second layer between each septum of the set of septa is substantially constant and a second pitch at the other of the first surface of the first layer or the first surface of the second layer between a first subset of the set of septa and a second subset of the set of septa is different.

12. The anti-scatter collimator of claim 11, wherein:
the set of septa are stacked in a first direction to define a stack having an end and a center, and
the pitch between the septa at the first surface of the second layer is non-constant moving from the end to the center.

13. An anti-scatter collimator comprising:
a first layer defining a first retaining member at a first surface, wherein the first layer has a first attenuation coefficient;
a second layer defining a second retaining member at a first surface that faces the first surface of the first layer, wherein the second layer has a second attenuation coefficient;
a plurality of septa disposed between the first layer and the second layer and physically contacting the first retaining member and the second retaining member, wherein:
the first retaining member and the second retaining member maintain a position of each of the plurality of septa relative to the first layer and the second layer, and
a pitch between a first septum of the plurality of septa and a second septum of the plurality of septa near the first layer is different than a second pitch between the first septum and the second septum of the plurality of septa near the second layer; and
a channel-shaped end support with a first support portion of the end support attached to the first layer, a second support portion of the end support attached to the second layer, and a third support portion of the end support extending between the first support portion and the second support portion, the third support portion abutting against an end of the septum such that linear movement of the septum is constrained by the third support portion only within one plane.

14. The anti-scatter collimator of claim 13, wherein:
a groove is defined in the first layer and extends from the first surface of the first layer toward a second surface of the first layer that is opposite the first surface of the first layer,
a first end of the first septum is disposed within the groove to maintain the position of the first septum relative to the first layer, the first end positioned between the first surface of the first layer and the second surface of the first layer.

15. The anti-scatter collimator of claim 14,
a second groove is defined in the second layer and extends from the first surface of the second layer toward a second surface of the second layer that is opposite the first surface of the second layer,
a second end of the first septum is disposed within the second groove to maintain the position of the first septum relative to the second layer, the second end positioned between the first surface of the second layer and the second surface of the second layer.

16. The anti-scatter collimator of claim 13, wherein the pitch is less than the second pitch.

17. The anti-scatter collimator of claim 13, wherein the second septum extends non-parallel to the first septum.

18. A computed tomography (CT) imaging modality, comprising:
a radiation source configured to emit radiation;
a detector array configured to detect at least a portion of the radiation; and
an anti-scatter collimator disposed between the radiation source and the detector array, the anti-scatter collimator comprising:
a first layer defining a first retaining member at a first surface, wherein the first layer has a first attenuation coefficient;
a second layer defining a second retaining member at a first surface that faces the first surface of the first layer, wherein the second layer has a second attenuation coefficient;
a septum disposed between the first layer and the second layer and physically contacting the first retaining member and the second retaining member, wherein:
the first retaining member and the second retaining member maintain a position of the septum relative to the first layer and the second layer, and
the septum has a third attenuation coefficient that is greater than the first attenuation coefficient and the second attenuation coefficient; and
a channel-shaped end support with a first support portion of the end support attached to the first layer, a second support portion of the end support attached to the second layer, and a third support portion of the end support extending between the first support portion and the second support portion, the third support portion abutting against an end of the septum such that linear movement of the septum is constrained by the third support portion only within one plane.

19. The CT imaging modality of claim 18, the first layer extending substantially parallel to the second layer.

20. The CT imaging modality of claim 18, the end support defining a window through which the septum is visible.

* * * * *